(12) United States Patent
Biato et al.

(10) Patent No.: US 10,881,602 B2
(45) Date of Patent: *Jan. 5, 2021

(54) COMPOSITION AND PROCESS FOR SHAPING OR ALTERING THE SHAPE OF HAIR

(71) Applicant: L'OREAL, Paris (FR)

(72) Inventors: Camila Maciel Biato, Rio de Janeiro (BR); Erika Alegrio Jarque Petali, Rio de Janeiro (BR); Serge Restle, Rio de Janeiro (BR); Liliane De Almeida Silvestre, Rio de Janeiro (BR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,111

(22) PCT Filed: Apr. 2, 2015

(86) PCT No.: PCT/BR2015/050037
§ 371 (c)(1),
(2) Date: Sep. 29, 2017

(87) PCT Pub. No.: WO2016/154692
PCT Pub. Date: Oct. 6, 2016

(65) Prior Publication Data
US 2018/0078487 A1    Mar. 22, 2018

(51) Int. Cl.
*A61K 8/894* (2006.01)
*A61K 8/46* (2006.01)
*A61Q 5/04* (2006.01)
*A61K 8/73* (2006.01)
*A45D 7/06* (2006.01)
(Continued)

(52) U.S. Cl.
CPC .............. *A61K 8/894* (2013.01); *A45D 7/06* (2013.01); *A61K 8/19* (2013.01); *A61K 8/41* (2013.01); *A61K 8/46* (2013.01); *A61K 8/731* (2013.01); *A61Q 5/04* (2013.01)

(58) Field of Classification Search
CPC .......... A61K 8/894; A61K 8/46; A61K 8/731
See application file for complete search history.

(56) References Cited

U.S. PATENT DOCUMENTS

2008/0025938 A1 * 1/2008 Cassier .................. A61K 8/447
424/70.5
2014/0261518 A1 * 9/2014 Savaides .................. A61K 8/65
132/206

FOREIGN PATENT DOCUMENTS

FR        2931659 A1      12/2009
JP        2007176898 A *   7/2007
WO       2006/056361 A1    6/2006

OTHER PUBLICATIONS

Angus Chemical Company "AMP-Ultra PC Specialty Neutralizers" <http://latinarnerica.in-cosmetics.com/_novadocuments/255482?v=636054135038200000> available May 2015; accessed Sep. 14, 2018 (Year: 2015).*

(Continued)

*Primary Examiner* — Nicole P Babson
(74) *Attorney, Agent, or Firm* — Polsinelli PC (57) ABSTRACT

Disclosed herein is a composition for shaping or altering the shape of hair, such as by straightening hair, wherein the composition contains a reducing agent, a neutralizing agent, a dimethicone copolyol, a cellulose compound, and water, wherein the pH of the composition ranges from about 2 to less than about 7. Also disclosed is a process for shaping or altering the shape of hair.

19 Claims, 1 Drawing Sheet

(51) Int. Cl.
*A61K 8/19* (2006.01)
*A61K 8/41* (2006.01)

(56) References Cited

OTHER PUBLICATIONS

English translation of Watanabe JP-2007176898-A (Year: 2007).*
Dow. DOWSIL SH 3771C Fluid <https://www.dow.com/en-us/pdp.dowsil-sh-3771-c-fluid.02507323z.html.> accessed Nov. 21, 2019 (Year: 2019).*
Ingredients <https://www.ingredientstodiefor.com/item/HydroxyEthylCellulose_HEC_/1333/> available Jul. 30, 2013; accessed Apr. 30, 2020 (Year: 2013).*
International Search Report and Written Report dated Jun. 19, 2015 issued in corresponding International Application No. PCT/BR2015/050037, 8 Pages.

\* cited by examiner

| Before Treatment | Rinsing | Not Rinsing |
|---|---|---|
| | | |
| Day of application | | |

COMPOSITION AND PROCESS FOR SHAPING OR ALTERING THE SHAPE OF HAIR

RELATED APPLICATIONS

This application is a national stage application (under 35 U.S.C. § 371) of PCT/BR2015/050037, filed Apr. 2, 2015, which is incorporated herein by reference in its entirety.

FIELD OF THE INVENTION

The present application relates to a composition and a process involving applying the composition onto hair for shaping or altering the shape of the hair, for example, by straightening the hair, wherein the composition contains a reducing agent, a neutralizing agent, a dimethicone copolyol, and a cellulose compound.

BACKGROUND OF THE INVENTION

Cosmetic and personal care products for use on keratinous substrates such as hair are available commercially in various forms, for example, as creams, lotions, gels, pastes, and powders. Regardless of the form, these products have to achieve and provide certain benefits and attributes such as efficaciousness, cosmeticity, desirable texture, stable formulations, and ease and convenience of use and application. Thus, in order to meet changing consumer needs and preferences, manufacturers of such products continuously seek to re-formulate and create new products with enhanced efficacy, while still remaining stable and safe to use. In addition, manufacturers continue to test the use of new raw materials and ingredients or new product forms that would help deliver the desired attributes and properties with respect to viscosity, texture, stability and efficacy.

One area where manufacturers are always seeking to improve in is in the area of hair cosmetic products such as those products designed to change the appearance, shape or configuration of hair. Examples of such hair cosmetic products are hair relaxers or hair straighteners which can relax or straighten curly or kinky hair, including wavy hair. Hair relaxers may either be applied in a hair salon by a professional or in the home by the individual consumer. Straightening or relaxing the curls of very curly hair may increase the manageability and ease of styling of such hair.

One type of composition that can be applied onto hair in order to change its shape and make it more manageable is an alkaline composition. Alkaline hair relaxing/straightening involves hydrolyzing the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, calcium hydroxide, organic hydroxides and other non-hydroxide compounds, for example, organic amines, generally fall under the category of no-lye products.

Still, it is desirable to find alternatives to the alkaline lye- and no-lye-based products and process described above which can damage the hair by weakening and/or causing dryness of the hair fibers. However, the discovery of new compositions and processes for changing the shape of hair that impart less or minimal damage to hair, may pose challenges to manufacturers and formulators because the incorporation of new ingredients into the compositions may negatively impacting their performance, cosmetic attributes, and formulation stability. In addition, the alkalinity and/or pH is an important consideration for these products. New processes of treating and changing the shape of hair may also impact the performance of the compositions, processing times and quality of use.

The present invention provides a composition for shaping or altering the shape of hair, such as by straightening the hair, containing a combination of a reducing agent, a neutralizing agent, a dimethicone copolyol, a cellulose compound, and water wherein the composition is non-alkaline such that its pH ranges from about 2 to less than about 7. The present invention also provides a process for shaping or altering the shape of hair, such as by straightening the hair, in an easy and efficacious manner, the process comprising applying onto the hair, said composition, brushing the hair, heating the hair while optionally applying a smoothing action on the hair, and rinsing the hair with water or contacting the hair with an intermediate agent having a neutral pH and selected from a shampoo and/or a conditioner, followed by rinsing with water. The hair can be contacted with a shampoo having a neutral pH, then rinsed with water before the composition is applied onto the hair.

It was surprisingly and unexpectedly discovered that the composition of the present invention is stable and has a viscosity that corresponds to a non-drip, and homogeneous consistency that facilitates the ease of application of the composition onto hair fibers, thereby resulting in an effective process of shaping or altering the shape of hair. In addition, the process of the invention allows good straightening/relaxing of hair while at the same time limiting the degradation of hair and maintaining an appreciated working quality, especially without excessive vaporization of the composition at the time of straightening. The hair treatment process according to the invention also makes it possible to minimize the problems of breaking of the hair fibers. The composition and the process of the invention were also found to improve the physical properties of the hair, by durably reducing the volume of the hair and the frizziness effect.

BRIEF SUMMARY OF THE INVENTION

The present invention relates to a composition for straightening hair comprising:
  (a) at least one reducing agent selected from thiol reducing agents, non-thiol reducing agents, and mixtures thereof;
  (b) at least one neutralizing agent;
  (c) at least one dimethicone copolyol which is present in an amount of from 0.5% to 5% by weight, preferably from 1% to 4% by weight, more preferably from 1.5% to 3% by weight, and even more preferably from 2% to 3% by weight;
  (d) from about 0.1% to about 2% by weight of at least one cellulose compound selected from hydroxyalkyl cellulose, alkylcellulose, and mixtures thereof; and
  (e) water;
wherein the pH of the composition ranges from 2 to less than 7;
all weights being based on the total weight of the composition.

The present invention also relates to process for shaping hair or altering the shape of hair, the process comprising the steps of:
  (1) applying onto the hair, the above-described composition;
  (2) brushing the hair;

(3) heating the hair at a temperature of at least 40° C.; while optionally applying a smoothing action on the hair; and (4) rinsing the hair with water or contacting the hair with an intermediate agent having a neutral pH and selected from a shampoo and/or a conditioner, followed by rinsing with water.

The hair can be contacted with a shampoo having a neutral pH, then rinsed with water before the composition in (1) is applied onto the hair Methods of making the compositions of the present invention are also disclosed in this disclosure.

According to the present invention, the composition of the invention is preferably in the form of a gel.

It is to be understood that both the foregoing general description and the following detailed description are exemplary and explanatory only, and are not restrictive of the invention.

BRIEF DESCRIPTION OF THE DRAWING

The FIGURE provides photographic images of hair samples, showing the straightening/shaping effects on hair imparted by the composition of the invention according to a rinsing protocol and a non-rinsing protocol.

DETAILED DESCRIPTION OF THE INVENTION

Figure 1:
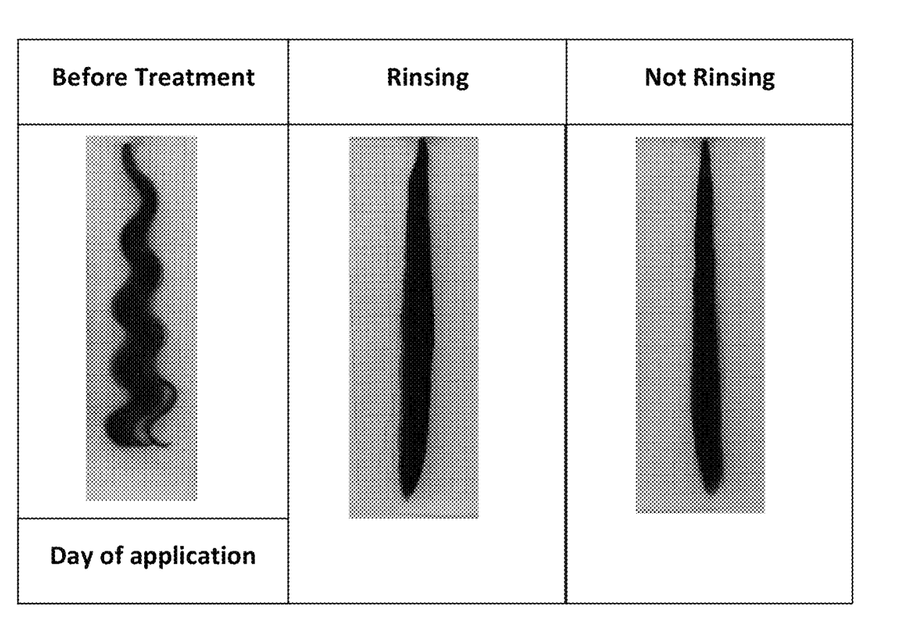

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−10% of the indicated number.

"Keratinous substrates" as used herein, include, but are not limited to skin, lips, and keratin or keratinous fibers such as hair and eyelashes.

"Volatile", as used herein, means having a flash point of less than about 100° C.

"Non-volatile", as used herein, means having a flash point of greater than about 100° C.

"Reducing agent" as used herein, means an agent capable of reducing the disulfide bonds of the hair.

"Active material" as used herein with respect to the percent amount of an ingredient or raw material, refers to 100% activity of the ingredient or raw material.

All numbers expressing pH values are to be understood as being modified in all instances by the term "about" which encompasses up to +/−3%.

The compositions and processes of the present invention can comprise, consist of, or consist essentially of the essential elements and limitations of the invention described herein, as well as any additional or optional ingredients, components, or limitations described herein or otherwise useful.

In one embodiment, the present invention relates to a composition for straightening hair comprising:

(a) from about 1% to about 15% by weight of least one reducing agent selected from thiolactic acid, thioglycolic acid, and mixtures thereof;

(b) at least one neutralizing agent selected from aminomethyl propanol and sodium hydroxide;

(c) from about 0.5% to about 5% by weight of at least one dimethicone copolyol;

(d) from about 0.3% to about 1.5% by weight of at least one cellulose compound comprising hydroxyethylcellulose; and (e) water;

all weights being based on the total weight of the composition;

wherein when the at least one neutralizing agent is selected from aminomethyl propanol, the aminomethyl propanol is present in an amount of from about 0.1% to about 6.3% by weight;

wherein when the at least one neutralizing agent is selected from sodium hydroxide, the sodium hydroxide is present in an amount of from about 0.1% to about 4.1% by weight;

wherein the pH of the composition ranges from 2 to less than 7; and wherein the composition is a gel.

In another embodiment, the present invention relates to a gel composition for straightening hair comprising:

(a) from about 4% to about 8% by weight of at least one reducing agent selected from thiolactic acid;

(b) at least one neutralizing agent;

(c) from about 1.5% to about 3% by weight of at least one dimethicone copolyol;

(d) from about 0.5% to about 1.5% by weight of hydroxyethylcellulose; and (e) water;

all weights being based on the total weight of the composition;

wherein the pH of the composition ranges from 2 to less than 7.

In yet another embodiment, the present invention relates to a gel composition for straightening hair comprising:

(a) from about 4% to about 8% by weight of at least one reducing agent selected from thiolactic acid;

(b) at least one neutralizing agent selected from aminomethyl propanol and sodium hydroxide;

(c) from about 2% to about 3% by weight of at least one dimethicone copolyol selected from oxypropylenated and/or oxyethylenated polydimethyl(methyl)siloxane, oxypropylenated and/or oxyethylenated polymethyl (C8-C22) alkyl dimethyl methyl siloxane, and mixtures thereof, and preferably selected from Dimethicone PEG-8 Benzoate, Dimethicone PEG-7 Phosphate, Dimethicone PEG-8 Phosphate, Dimethicone PEG-10 Phosphate, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-17/18 Dimethicone, cetyl PEG/PPG-10/1 dimethicone, and mixtures thereof;

(d) from about 0.75% to about 1.25% by weight of at least one cellulose compound selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose), hydroxypropylmethylcellulose (also known as HPMC), cetyl hydroxyethylcellulose, methylcellulose, ethylcellulose, ethylhexylcellulose, and mixtures thereof; and (e) water;

all weights being based on the total weight of the composition;

wherein the pH of the composition ranges from 2 to less than 7.

In certain embodiments, the dimethicone copolyol is preferably PEG-12 dimethicone.

In an embodiment, the present invention relates to a process for straightening hair, the process comprising the steps of:

(1) contacting hair with a shampoo having a neutral pH;
(2) rinsing the hair with water;
(3) applying onto the hair, a composition containing:
(a) least one reducing agent selected from thiol reducing agents, non-thiol reducing agents, and mixtures thereof and present in an amount of from 1% to 15% by weight, preferably from 3% to 10% by weight, more preferably from 4% to 8% by weight;
(b) at least one neutralizing agent selected from aminomethyl propanol and sodium hydroxide;
(c) at least one dimethicone copolyol which is present in an amount of from 0.5% to 5% by weight, preferably from 1% to 4% by weight, more preferably from 1.5% to 3% by weight, and even more preferably from 2% to 3% by weight;
(d) from about 0.1% to about 2% by weight of at least one cellulose compound selected from hydroxyalkyl cellulose, alkyl cellulose, and mixtures thereof; and
(e) water;
wherein the pH of the composition ranges from 2 to less than 7;
all weights being based on the total weight of the composition;
wherein when the at least one neutralizing agent is selected from aminomethyl propanol, the aminomethyl propanol is present in an amount of from 0.3% to 4.6% by weight; and
wherein when the at least one neutralizing agent is selected from sodium hydroxide, the sodium hydroxide is present in an amount of from 1% to 3% by weight;
(4) brushing the hair;
(5) heating the hair at a temperature of at least 40° C.; while optionally applying a smoothing action on the hair; and
(6) rinsing the hair with water or contacting the hair with an intermediate agent having a neutral pH and selected from a shampoo and/or a conditioner, followed by rinsing with water.

Preferably, the above-described process comprises the steps of:

(1) First, contacting hair with a shampoo having a neutral pH;
(2) Second, rinsing the hair with water;
(3) Third, applying onto the hair, any one of the above-described compositions of the invention;
(4) Fourth, brushing the hair;
(5) Fifth, heating the hair at a temperature of at least 40° C.; while optionally applying a smoothing action on the hair; and
(6) Sixth, heating the hair at a temperature of at least 40° C.; while optionally applying a smoothing action on the hair.

In certain embodiments, the heating step in any one of the above-described processes of the invention is preferably accomplished by use of device such as a heating flat iron device, a blow dryer, or a hair dryer. When a hair dryer or blow dryer is used, a brush or comb may be passed one or more times over or through the hair.

The heating step in any one of the above-described processes of the invention may also be accompanied by a smoothing action on the hair, preferably performed with a mechanical or physical device, for example, the plates of a flat iron or a hair brush.

In certain embodiments, the heating step in any one of the above-described processes is accomplished at a temperature higher than 100° C.

In certain embodiments, the composition in any one of the above-described processes of the invention is allowed to remain on the hair for a predetermined amount of time sufficient to shape or alter the shape of the composition.

In preferred embodiments, the composition in any one of the above-described processes of the invention is a hair straightening composition. In yet other preferred embodiments, said hair straightening composition is allowed to remain on the hair for a predetermined amount of time sufficient as to achieve a desired degree of hair straightening.

The compositions in the above-described process are stable over time, that is, they do not exhibit phase separation and they can be stored for several months without modification and with very little change or fluctuation in the viscosity and/or rheology and pH of the composition.

It was surprisingly and unexpectedly discovered that the application of the compositions of the present invention, resulted in effectively shaped or straightened hair.

It was also surprisingly and unexpectedly discovered that the composition of the invention was stable over time and had a smooth, non-drip, and homogenous texture/consistency and effectively shaped or straightened hair.

The non-drip consistency of the compositions of the present invention is desirable because it helps the compositions to remain on the hair for a predetermined amount of time as to achieve the desired shape of the hair or desired degree of straightening of the hair.

Reducing Agent

The present invention employs at least one reducing agent selected from thiol or non-thiol reducing agents.

Thiol reducing agents which can be used in the composition of the invention include thiol reducing agents selected from thiolactic acid, thioglycolic acid, cysteine, cysteamine, homocystine, glutathione, thioglycerol, thiomalic acid, 2-mercaptopropionic acid, 3-mercaptopropionic acid, thiodiglycol, 2-mercaptoethanol, dithiothreitol, thioxanthine, thiosalicylic acid, thiopropionic acid, lipoic acid, N-acetylcysteine, their salts thereof, and mixtures thereof.

Non-thiol reducing agents which can be used in the composition of the invention include in particular alkali metal, alkaline-earth metal sulfites, hydrides or phosphines, and mixtures thereof.

In some embodiments, the reducing agent or agents used in the composition of the invention are thiol reducing agents, more particularly thioglycolic acid and thiolactic acid or their salts thereof, especially alkali metal, alkaline-earth metal or ammonium salts, cysteine, and mixtures thereof.

In yet other embodiments, the reducing agent used in the composition of the invention is chosen from thiolactic acid, thioglycolic acid, and mixtures thereof In certain embodiments, the reducing agent used in the composition of the invention is thiolactic acid.

In other embodiments, the reducing agent used in the composition of the invention is thioglycolic acid.

In yet other embodiments, the reducing agent used in the composition of the invention comprises thiolactic acid and thiolgycolic acid.

The at least one reducing agent can be employed in the composition of the present invention in an amount of from about 1% to about 15% by weight, preferably from about 3% to about 10% by weight, more preferably from about 4% to about 8% by weight, based on the total weight of the composition, including all ranges and subranges therebetween.

In certain embodiments, the at least one reducing agent is selected from thiolactic acid and is employed in the composition of the present invention in an amount of about 1%, or about 2%, of about 3%, or about 4%, or about 5%, of about 5.5%, or about 6%, or about 6.5%, or about 7%, or about 7.5%, or about 8%, by weight, based on the total weight of the composition.

Dimethicone Copolyol

The present invention employs at least one dimethicone copolyol.

Dimethicone Copolyol, as used herein, includes a polymer made from dimethicone and polyoxyethylene and/or polyoxypropylene.

Suitable examples of dimethicone copolyols include Dimethicone PEG-8 Adipate, Dimethicone PEG-8 Benzoate, Dimethicone PEG-7 Phosphate, Dimethicone PEG-8 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and mixtures thereof.

Dimethicone copolyols can also be described as silicone surfactants or as emulsifiers.

While not wishing to be bound to any one theory, it is believed by the inventors that the use of dimethicone copolyols in the compositions of the invention help stabilize the composition.

Thus, the dimethicone copolyol employed according to the invention is advantageously an oxypropylenated and/or oxyethylenated polydimethyl(methyl)siloxane. Use may be made, as dimethicone copolyol, of those corresponding to the following formula (I):

in which:
R1, R2 and R3 represent, independently of one another, a C1-C6 alkyl radical or a —(CH2)x-(OCH2CH2)y-(OCH2CH2CH2)z-OR4 radical, at least one Rb R2 or R3 radical not being an alkyl radical; R4 being a hydrogen, a C1-C3 alkyl radical or a C2-C4 acyl radical;
A is an integer ranging from 0 to 200;
B is an integer ranging from 0 to 50; provided that A and B are not equal to zero at the same time; x is an integer ranging from 1 to 6; y is an integer ranging from 1 to 30; z is an integer ranging from 0 to 5.

According to a preferred embodiment of the invention, in the compound of formula (I), R=R3=methyl radical, x is an integer ranging from 2 to 6 and y is an integer ranging from 4 to 30. R4 is in particular a hydrogen.

Mention may be made, as examples of compounds of formula (I), of the compounds of formula (II):

in which A is an integer ranging from 20 to 105, B is an integer ranging from 2 to 10 and y is an integer ranging from 10 to 20.

Mention may also be made, as examples of silicone compounds of formula (I), of the compounds of formula (III):

in which A' and y are integers ranging from 10 to 20.

Use may be made, as dimethicone copolyol, of those sold under the names DC 5329, DC 7439-146, DC 2-5695 and Q4-3667 by Dow Corning; and KF-6013, KF-6015, KF-6016, KF-6017 and KF-6028 by Shin-Etsu.

In an embodiment, the compositions of the invention comprise as dimethicone copolyol one of those sold under the names KF-6013, KF-6015, KF-6016, KF-6017 and KF-6028 by Shin-Etsu.

In another embodiment, the dimethicone copolyol in the compositions of the invention is chosen from PEG-12 dimethicone commercially available from Dow Corning under the trade name XIAMETER® OFX-0193 FLUID.

The dimethicone copolyols in the compositions of the invention can also be chosen from at least one C8-C22 alkyl dimethicone copolyol.

This C8-C22 alkyl dimethicone copolyol of the invention is more particularly an oxypropylenated and/or oxyethylenated polymethyl (C8-C22) alkyl dimethyl methyl siloxane.

The C8-C22 alkyl dimethicone copolyol is advantageously a compound of the following formula (IV):

wherein:
PE represents from groups (—C2H4O)x-(C3H6O)y-R, wherein R is chosen from a hydrogen atom and an alkyl radical comprising from 1 to 4 carbon atoms, x is an integer ranging from 0 to 100, and y is an integer ranging from 0 to 80, provided that x and y are not simultaneously equal to 0; and
m is an integer ranging from 1 to 40, n is an integer ranging from 10 to 200, o is an integer ranging from 1 to 100, p is an integer ranging from 7 to 21, and q is an integer ranging from 0 to 4.

Preferably, R is a hydrogen atom, m is an integer ranging from 1 to 10, n is an integer ranging from 10 to 100, o is an integer ranging from 1 to 30, p is 15, and q is 3. In a preferred embodiment the at least one C8-C22 alkyl dimethicone copolyol of the present invention is chosen from cetyl dimethicone copolyols such as the product marketed under the name Abil® EM-90 by the company Goldschmidt.

In one embodiment, the C8-C22 alkyl dimethicone copolyol is a cetyl dimethicone copolyol, and more particularly the product marketed under the name Abil® EM-90 by the company Goldschmidt (also known as cetyl PEG/PPG-10/1 dimethicone).

In another embodiment, the compositions of the invention comprise cetyl PEG/PPG-10/1 dimethicone as C8-C22 alkyl dimethicone copolyol and a mixture of dimethicone and dimethicone/vinyl dimethicone crosspolymer as organopolysiloxane elastomer not containing a hydrophilic chain.

In another preferred embodiment, the compositions of the invention comprise a mixture of dimethicone and dimethicone/vinyl dimethicone crosspolymer as organopolysiloxane elastomer not containing a hydrophilic chain, a PEG-10 dimethicone as dimethicone copolyol, and a cetyl PEG/PPG-10/1 dimethicone as C8-C22 alkyl dimethicone copolyol.

Thus, in certain embodiments, the dimethicone copolyol in the present invention is chosen from oxypropylenated and/or oxyethylenated polydimethyl(methyl)siloxane, oxypropylenated and/or oxyethylenated polymethyl (C8-C22) alkyl dimethyl methyl siloxane, and mixtures thereof.

In certain other embodiments, the dimethicone copolyol is chosen from Dimethicone PEG-8 Benzoate, Dimethicone PEG-7 Phosphate, Dimethicone PEG-8 Phosphate, Dimethicone PEG-10 Phosphate, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-17/18 Dimethicone, cetyl PEG/PPG-10/1 dimethicone, and mixtures thereof. In other embodiments, the dimethicone copolyol is preferably PEG-12 dimethicone, The dimethicone copolyols are generally present in the composition in a proportion as active material (AM) ranging from about 0.5% to about 5% by weight, preferably from about 1% to about 4% by weight, more preferably from about 1.5% to about 3% by weight, even more preferably from about 2% to about 3% by weight, based on the total weight of the composition, including all ranges and subranges therebetween.

In certain embodiments, the dimethicone copolyols are employed in the compositions of the present invention in an amount of about 0.1%, or about 0.25%, or about 0.5%, or about 0.75%, or about 1% by weight, or about 1.1%, or about 1.2%, or about 1.3%, or about 1.4% by weight, or about 1.5% by weight, or about 1.6%, or about 1.7%, or about 1.8%, or about 1.9% by weight, or about 2% by weight, based on the total weight of the composition.

Neutralizing Agent

Suitable neutralizing agents are other than the at least one salt described above and may be selected from alkali metal carbonates, alkali metal phosphates, organic amines, hydroxide base compounds, and mixtures thereof, particularly from organic amines, alkali metal hydroxides, alkali earth metal hydroxides, and mixtures thereof.

Organic amines may be selected from amino-2-methyl-1-propanol (or aminomethyl propanol), ethylamines, ethyleneamines, alkanolamines, cyclic amines and other cyclic compounds, saturated or unsaturated, having one or more nitrogen atoms within the ring, and mixtures thereof.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

The at least one neutralizing agent may be chosen from at least one organic amine such as at least one alkanolamine. Particularly preferred alkanolamines are 2-amino-2-methyl-1-propanol (aminomethyl propanol), ethanolamine (also known as monoethanolamine or MEA), triethanolamine, and mixtures thereof. An even more particularly preferred alkanolamine is ethanolamine.

According to at least one embodiment, the at least one neutralizing agent is chosen from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

According to another preferred embodiment, the at least one neutralizing agent is chosen from aminomethyl propanol, sodium hydroxide, lithium hydroxide, calcium hydroxide, and mixtures thereof.

In one preferred embodiment, the at least one neutralizing agent is selected from aminomethyl propanol and is present in an amount of from about 0.1% to about 6.3% by weight, preferably from about 0.2% to about 5.5% by weight, more preferably from about 0.3% to about 5% by weight, even more preferably from about 0.3% to about 4.6% by weight, based on the total weight of the composition, including all ranges and subranges therebetween.

In certain embodiments, the at least one neutralizing agent selected from aminomethyl propanol is employed in the compositions of the present invention in an amount of about 0.1%, 0.3%, 0.4%, 0.5%, 0.6%, 0.7%, 0.8%, 0.9%, 1%, 1.3%, 1.4%, 1.5%, 1.75%, 2%, 2.3%, 2.4%, 2.5%, 2.75%, or 3%, 3.3%, 3.5%, 3.75%, 4%, 4.3%, 4.5%, 4.6%, by weight, based on the total weight of the composition.

In another preferred embodiment, the at least one neutralizing agent is selected from sodium hydroxide and is present in an amount of from about 0.1% to about 4.1% by weight, preferably from about 0.15% to about 3.5% by weight, more preferably from about 0.2% to about 3% by weight, even more preferably from about 1% to about 3% by weight, based on the total weight of the composition, including all ranges and subranges therebetween.

In certain embodiments, the at least one neutralizing agent selected from sodium hydroxide is employed in the compositions of the present invention in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, about 2.3%, 2.4%, 2.5%, 2.6%, 2.7%, 2.8%, 2.9%, 3%, based on the total weight of the composition.

Cellulose Compound

The compositions according to various embodiments of the disclosure also comprise at least one cellulose compound chosen from hydroxyalkyl cellulose, alkylcellulose, and mixtures thereof. In certain embodiments, the at least one cellulose compound is used as a thickening or viscosity agent in the compositions of the present invention In some embodiments, the at least one cellulose compound is chosen from hydroalkyl celluloses. Suitable examples of the hydroxyalkyl cellulose of the present invention may be chosen from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), and mixtures thereof.

Other suitable examples of the at least one hydroxyalkyl cellulose compound of the present invention include hydroxyalkyl celluloses modified with groups comprising at least one fatty chain; examples that may be mentioned include:—hydroxyethyl celluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyls or cetyl hydroxyethylcellulose) sold by the company Aqualon, or the product Bermocoll EHM 100® sold by the company Berol Nobel,—hydroxyethyl celluloses modified with alkylphenyl polyalkylene glycol ether groups, such as the product Amercell Polymer HM-1500® (polyethylene glycol (15) nonylphenyl ether) sold by the company Amerchol.

Other suitable examples of the at least one hydroxyalkyl cellulose compound of the present invention are hydroxyalkyl celluloses optionally modified with a hydrophobic group, such as hydroxyethylcelluloses and hydroxymethylcelluloses optionally modified with a hydrophobic group.

In other embodiments, the at least one cellulose compound is chosen from alkyl cellulose. Suitable alkylcelluloses of the present invention may be chosen from methylcellulose, ethylcellulose, ethylhexylcellulose, and mixtures thereof.

In certain embodiments of the invention, the at least one cellulose compound is chosen from hydroxyethylcellulose which is commercially available under the tradename CELLOSIZE HYDROXYEHTYL CELLULOSE PCG-10 as sold by the company The Dow Chemical.

In yet other embodiments, the at least one cellulose compoundis is chosen from methyl hydroxyethylcellulose which is commercially available under the tradename of STRUCTURE® CEL 8000 M as sold by Akzo Nobel.

The amount of thickening agent in the composition used in the invention may be between 0.1% and 2% by weight, preferably between 0.5% and 1.5% by weight, or more preferably from about 0.5% to about 1% by weight, based on the total amount of the composition (percentage of active material), including all ranges and subranges therebetween.

In certain embodiments, the at least one thickening agent is employed in the compositions of the present invention in an amount of about 0.1%, 0.2%, 0.3%, 0.4%, 0.5%, 0.6%, 0.7%, 0.75%, 0.8%, 0.9%, 1%, 1.1%, 1.2%, 1.3%, 1.4%, 1.5%, 1.6%, 1.7%, 1.8%, 1.9%, 2% by weight, based on the total weight of the composition.

Without wishing to be bound to any one theory, it is believed by the inventors that the use of at least one thickening agent in the composition of the invention results in a composition with a desirable, non-drip consistency or thickness/viscosity while still remaining easy to apply and spread on a substrate such as keratin fibers (e.g., hair).

Water

The compositions of the present invention contain water. Water can be present in the amount of about 95%, 92%, 90%, 89%, 88%, 87%, 85%, 84%, 83%, 82%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 88% by weight, relative to the weight of the compositions.

In other embodiments, water can be present in the compositions of the present invention in the amount of at least about 95%, 92%, 90%, 89%, 88%, 87%, 85%, 84%, 83%, 82%, 80%, 70%, 60%, 50%, 40%, 30%, 20%, 10%, 5% by weight or less, based on the total weight of the compositions.

Cosmetically Acceptable Solvent

The compositions of the present invention may further comprise at least one cosmetically acceptable solvent chosen from organic solvents.

Suitable organic solvents may be chosen from volatile and nonvolatile organic solvents.

Suitable organic solvents are typically C2-C8 alcohols, glycols, polyols, polyol ethers, glycol ethers, glycerin, hydrocarbons, oils, and mixtures thereof. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL™ DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxy-silicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In certain embodiments of the present invention, the at least one organic solvent is chosen from ethanol.

Intermediate Agent

The intermediate agent of the present invention may be any shampoo or conditioner composition. Preferably, the intermediate agent has a neutral pH.

Auxiliary Ingredients

The compositions according to the invention may further comprise any auxiliary ingredient usually used in the field under consideration, selected, for example, from conditioning agents, natural and synthetic oils, humectants, shine agents, fillers, colorants, pigments, chelating agents, sequestering agents, fragrances, preservatives, stabilizers, and mixtures thereof.

It is a matter of routine operations for a person skilled in the art to adjust the nature and amount of the additives present in the compositions in accordance with the invention such that the desired cosmetic properties and stability properties thereof are not thereby affected.

pH

In certain embodiments, the neutralizing agent is used in an amount such that the pH of the compositions of the invention is from about pH 2 to less than about 7, preferably, from about pH 2 to about 6.5, or more preferably from about pH 2 to about 6 or from about pH 2 to about 4, including all ranges and subranges there-between.

In some embodiments, the neutralizing agent is used in an amount such that the pH of the compositions of the invention is from about 2 to 6, including all ranges and subranges there-between.

In other embodiments, the neutralizing agent is used in an amount such that the pH of the compositions of the invention is from about 2 to 4, including all ranges and subranges there-between.

In certain other embodiments, the pH of the compositions of the invention is about 2, 2.5, 3, 3.5, 4, 4.5, 5, 5.5, 6, 6.5. pH can be adjusted with acidic agents other than the thiol-based reducing agents of the invention such as mineral acids, chlorhydric acid or phosphoric acid, or with basic agents such as mineral basic agents as ammonia, carbonates, bicarbonates, hydroxides or organic basic agents such as alcanolamines All numbers expressing pH values are to be understood as being modified in all instances by the term "about" which encompasses up to +/−0.2. For example, a pH value of about 7.0 refers to 7+/−0.2.

The compositions of the present invention are in the form of a gel.

In other embodiments, the composition of the present invention has a viscosity of from about 60 M2 to about 70 M2, preferably from about 62 M2 to about 68 M2, more preferably from about 62 M2 to about 65 M2, as measured by a Rheomat RM180 at 25° C.

In certain preferred embodiments, the composition of the present invention has a viscosity of from about 62 M2 to about 65 M2 and a pH ranging from about pH 2 to about 6.

In some preferred embodiments, the composition of the present invention has a viscosity of from about 62 M2 to about 65 M2 and a pH ranging from about pH 2 to about 4.

All numbers expressing viscosity values are to be understood as being modified in all instances by the term "about" which encompasses up to +/−0.2. For example, a viscosity value of about 64.2 M2 refers to 64.2+/−0.2 M2.

In preferred embodiments, the composition of the present invention is a hair straightening composition.

The composition of the present invention is stable such that the straightening efficacy of the composition is preserved until the composition is ready to be used.

In addition, the compositions of the present invention did not exhibit phase separation.

Methods of Making

The compositions of the present invention are made by combining at least one reducing agent, at least one neutralizing agent, at least one dimethicone copolyol, at least one cellulose, and water.

In one embodiment, the method of making the compositions of the present invention comprises the steps of:
 (1) combining:
 (a) least one reducing agent selected from thiol reducing agents, non-thiol reducing agents, and mixtures thereof;
 (b) at least one neutralizing agent;
 (c) at least one dimethicone copolyol;
 (d) from 0.1% to 2% by weight of at least one cellulose compound chosen from hydroxyalkyl cellulose, alkylcellulose, and mixtures thereof; and
 (e) water;
 all weights being based on the total weight of the composition; and
 (2) mixing (a) to (e) in order to form a composition having a pH ranging from 2 to less than 7.

The invention also concerns a process of shaping or altering the shape of hair, for example, by straightening hair. The process comprises the steps of:
 (1) applying onto the hair, a composition containing:
 (a) least one reducing agent selected from thiol reducing agents, non-thiol reducing agents, and mixtures thereof, preferably selected from thiolactic acid, thioglycolic acid, and mixtures thereof, and more preferably selected from thiolactic acid;

(b) at least one neutralizing agent, preferably selected from aminomethyl propanol, sodium hydroxide, and mixtures thereof;

(c) at least one dimethicone copolyol;

(d) from 0.1% to 2% by weight of at least one cellulose compound chosen from hydroxyalkyl cellulose, alkylcellulose, and mixtures thereof, preferably chosen from hydroxyehtylcellulose; and (e) water;

wherein the pH of the composition ranges from 2 to less than 7;

all weights being based on the total weight of the composition;

(2) brushing the hair;

(3) heating the hair at a temperature of at least 40° C., preferably at a temperature of from about 40° C. to about 250° C., preferably from about 100° C. to about 230° C., or more preferably from about 150° C. to about 230° C.; while optionally applying a smoothing action on the hair, wherein when a smoothing action is employed, the heating action and smoothing action are accomplished by use of a heating flat iron device; and (4) rinsing the hair with water or contacting the hair with an intermediate agent having a neutral pH, followed by rinsing with water.

Preferably, before the composition in the process above is applied onto the hair, the hair is first contacted with a shampoo having a neutral pH and then rinsed with water.

In certain embodiments, the intermediate agent in the process above is a shampoo or conditioner, preferably having a neutral pH.

In certain embodiments, the composition is allowed to remain (leave-on time) on the keratin fibers for a pre-determined amount of time, for example, from about 1 to about 60 minutes, or such as from about 5 to about 45 minutes, or such as from about 5 to about 30 minutes, or such as from about 10 to about 20 minutes, or such as at about 20 minutes, or such as at about 10 minutes. The pre-determined amount of time is sufficient to achieve satisfactory straightening or shaping or altering the shape of the keratin fibers such as hair on the human head.

In other embodiments, the composition is rinsed from the hair with water before brushing the hair. The rinsed hair may also be subjected to a detangling or smoothing action before brushing the hair.

Suitable devices for detangling or brushing or smoothing the hair include a hair brush, comb, or heating flat iron. The smoothing or detangling action on the hair may also include running the fingers through the hair.

The composition can also be applied onto the hair using an applicator device or with the hands or gloved hands.

A suitable applicator device is an applicator brush or applicator comb or applicator spatula or a dispenser or applicator tip attached to the container holding the composition.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition present on the fibers or hair is left in place for a time, generally, from about 1 to about 60 minutes, such as from about 5 to about 45 minutes, or such as from about 5 to about 20 minutes, or such as from about 10 to about 20 minutes, or such as of about 20 minutes or such as of about 10 minutes.

It has been surprisingly and unexpectedly discovered that the compositions of the present invention have a non-drip consistency that is still easy to spread on keratin fibers, such as hair.

It has surprisingly and unexpectedly discovered that the application of the composition onto the fibers results in satisfactory straightening of hair.

The straightening effects obtained using the compositions and process of the present disclosure may also be durable or wash resistant.

The degree of straightening the hair may be evaluated by visually assessing the reduction in curliness and/or waviness and/or frizziness of the hair after contacting the hair with the composition of the invention. Another type of evaluation can also involve measuring the length of the hair as well as the width of the bulk of hair before and after contacting the hair with the composition.

It was surprisingly and unexpectedly discovered that the hair contacted with the compositions of the invention did not feel as rough and visually appeared to be more smooth, extended and straight compared to hair contacted with conventional or traditional straightening compositions.

The compositions of the present invention may be packaged in any suitable container such as a tube, a jar or a bottle. In certain embodiments, the composition can be packaged in a tube or bottle, for example, a squeeze tube or squeeze bottle. Additionally, an applicator device can be attached or connected to the opening of the packaging/squeeze tube or bottle wherein the applicator device is a brush or a comb with teeth such that the ends of the teeth have openings from which the composition of the invention can flow through and be applied directly onto the hair.

The composition of the present invention may also be provided as component of a kit for shaping or altering the shape of hair wherein the kit can additionally contain other components such as an intermediate agent having a neutral pH chosen from a shampoo or a conditioner.

As used herein, the process and composition disclosed herein may be used on the hair that has not been artificially dyed, pigmented or permed.

As used herein, the process and composition disclosed herein may be also used on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Example 1: Compositions

TABLE 1

Inventive Composition (Gel)

| INCI US | Formula A, % by weight |
|---|---|
| AMINOMETHYL PROPANOL | 2 |
| THIOLACTIC ACID | 8 |
| HYDROXYETHYLCELLULOSE | 0.75 |
| CELLULOSE PCG-10 (AMERCHOL/DOW CHEMICAL) | |
| PEG-12 DIMETHICONE | 2 |
| WATER | Q.S. to 100 |

TABLE 2

Comparative Compositions (Gel):

| INCI US | Formula B, % by weight pH = 3.51 | Formula C, % by weight pH = 3.54 | Formula D, % by weight pH = 3.51 | Formula E, % by weight pH = 3.51 |
|---|---|---|---|---|
| AMINOMETHYL PROPANOL | 3 | 3 | 3 | 3 |
| THIOLACTIC ACID | 8 | 8 | 8 | 8 |
| HYDROXYETHYLCELLULOSE CELLOSIZE HYDROXYETHYL CELLULOSE PCG-10 (AMERCHOL/DOW CHEMICAL) | 0.75 | 0.75 | 0.75 | 0.75 |
| DIMETHICONE, 80% (and) AMODIMETHICONE, 20% KF 8020 (SHIN ET SU) | 2 | — | — | — |
| DIMETHICONE | — | 2 | — | — |
| AMODIMETHICONE IN EMULSION (57.5% ACTIVE) | — | — | 2 | — |
| CYCLOPENTASILOXANE (85.3% BY WEIGHT) DIMETHICONOL (14.7% BY WEIGHT) | — | — | — | 2 |
| WATER | QS 100 | QS 100 | QS 100 | QS 100 |

The compositions above were each prepared according to the general procedure:

2. Heat water to about 70° C.
3. Add the cellulose material and keep the temperature at about 70° C. and agitate the mixture for 30 minutes.
4. Add the silicone material and mix for another 15 minutes at 70° C.
5. Cool to 25° C.
6. Add the neutralizing agent at 25° C. with agitation and then add the thiolactic acid.
7. Adjust the pH and check the viscosity.

The viscosity of the inventive composition was measured using the Mettler RM 180 Rheomat, viscometer spindle #2, at 25° C. (uD=Units of Deflection).

A viscosity measurement in M2 units ranging up from about 60 to 65 M2 corresponded to a texture and consistency of a gel composition. The gel texture provided the benefits of ease of application of the composition into the hair, spreadability of the composition on the hair, and/or ease of brushing or combing the hair. The inventive composition with the gel texture also did not readily drip off the hair contacted with the composition and remained on the hair during the straightening processing time.

The consistency and texture of the inventive formulas allow for the formulas to be packaged jars, in tubes (e.g., squeeze tubes) or bottles (eg, applicator bottles).

The inventive formula was also found to be stable. Stability was measured by placing the formulas in a humidity-controlled environment set at 4° C., 25° C. and 45° C. for at least 2 months. The formula was considered to be stable when no phase separation is observed and there were very little fluctuations in viscosity and pH.

Example 2: Processes for Straightening or Altering the Shape of Hair and Assessments of Straightening Performance Processes for Straightening Hair These studies were conducted on curly or wavy hair swatches (virgin hair, i.e., not chemically treated) using the inventive compositions and the comparative compositions.

The process of straightening the hair was performed according to a rinsing protocol (Process 1) and a non-rinsing protocol (Process 2).

For Process 1, the following steps were followed:
1. the hair was contacted with a shampoo (neutral pH);
2. the hair was rinsed with water;
3. the test composition (Inventive or comparative) was applied onto the hair using an applicator brush device (approximately 1 gram of the composition per gram of hair or approximately 300 grams per head of hair);
4. the test composition was allowed to remain on the hair for thirty minutes;
5. the hair was brushed with a hair brush using 20 to 30 strokes;
6. the hair was smoothed and heated with a flat iron set at 230° C. and using 10 strokes (or passes);
7. the hair was contacted with a shampoo and/or a conditioner (neutral pH);
8. the hair was rinsed with water (if shampoo is used in step 7, then this rinsing step can optionally, be followed by a step of contacting the hair with a conditioner having neutral pH, and then rinsing with water);
9. the shampoo/rinse/optional conditioning/rinse cycle was repeated as many times as desired.

For Process 2, the following steps were followed:
1. the hair was contacted with a shampoo (neutral pH);
2. the hair was rinsed with water;
3. the test composition (Inventive or comparative) was applied onto the hair using an applicator brush device (approximately 1 gram of the composition per gram of hair or approximately 300 grams per head of hair);

4. the test composition was allowed to remain on the hair for thirty minutes;

5. the test composition was rinsed off the hair;

6. the hair was brushed with a hair brush using 20 to 30 strokes;

7. the hair was smoothed and heated with a flat iron set at 230° C. and using 10 strokes (or passes);

8. the hair was contacted with a shampoo and/or a conditioner (neutral pH);

9. the hair was rinsed with water; (if shampoo is used in step 7, then this rinsing step can optionally, be followed by a step of contacting the hair with a conditioner having neutral pH, and then rinsing with water);

10. the shampoo/rinse/optional conditioning/rinse cycle was repeated as many times as desired.

Assessments of Straightening Performance and Reduction of Frizziness and Volume of Hair Straightening performance on hair was visually assessed for the following attributes: reduction of the volume (width) of the hair (also indicative of the degree of frizziness of and degree of discipline of the hair) and degree of straightening of the hair swatch. These attributes can also be measured or assessed on a 1 to 4 scale, with 4 being the smallest volume which indicates the greatest degree of straightening or lengthening of the hair, greatest reduction in frizziness or volume of the hair and greatest amount of discipline of the hair.

The FIGURE shows images of hair swatches before treating the swatch with the inventive composition, formula A, after treating a swatch with formula A by subjecting the swatch to the above-described rinsing protocol (process 1), and after treating a swatch with formula A by subjecting the swatch to the above-described non-rinsing protocol (process 2), It was found that the inventive formula significantly straightened the hair from a curly state, imparted excellent discipline to the hair (i.e., very low amount of or no frizz) and significantly reduced the volume of the hair.

In comparison to the comparative formulas in table 2, it was observed that while visually, the degree of straightening and/or discipline and/or volume reduction was comparable for all formulas (inventive and comparative), the hair treated with the inventive composition had better or increased natural feel to the touch. Furthermore, the use of hydroxyethylcellulose in the inventive composition improved the quality and process of straightening the hair, i.e, it was easier to brush the hair and the flat iron plates slid/passed better or easier over the hair.

Example 3: Testing Various Ingredients Employed in the Inventive Formula

A. Testing different neutralizing agents (sodium hydroxide and aminomethyl propanol) in aqueous solutions containing 8% by weight thiolactic acid at different pH values on curly or wavy hair swatches (virgin hair, i.e., not chemically treated) using Process 1

TABLE 3

| Sodium Hydroxide | | | | | | |
|---|---|---|---|---|---|---|
| | pH value | | | | | |
| | 2 | 4 | 6 | 8 | 10 | 12 |
| % by wt of sodium hydroxide | 0.2 | 2.0 | 3.0 | 3.8 | 4.4 | 6.3 |
| Straightening performance | 3.5 | 3.5 | 3.5 | 2.0 | — | — |

At pH values of 8 to 12, a high level of sensitization was observed; hair breakage was also observed in this pH range. As such, the hair was not rated for straightening performance at pH values of 10 and 12. At pH values of 2 to 6, hair cosmeticity and discipline was improved.

TABLE 4

| Aminomethyl Propanol | | | | | | |
|---|---|---|---|---|---|---|
| | pH value | | | | | |
| | 2 | 4 | 6 | 8 | 10 | 12 |
| % by wt of Aminomethyl Propanol | 0.3 | 4.6 | 6.5 | 7.0 | 15.8 | 30.0 |
| Straightening performance | 3.5 | 3.5 | 1.5 | 2.5 | — | — |

At pH values of 6 to 12, a high level of sensitization was observed; hair breakage was also observed in this pH range. The hair was not rated for straightening performance at pH values of 10 and 12. At pH values of 2 to 4, hair cosmeticity and discipline was improved; the hair also felt natural to the touch.

B. Swatch evaluation using different concentrations of Thiolactic acid in aqueous solutions having similar pH values on curly or wavy hair swatches (virgin hair, i.e., not chemically treated)

TABLE 5

| Thiolactic Acid | | | |
|---|---|---|---|
| pH value | 3.51 | 3.54 | 3.51 |
| % by weight thiolactic acid | 4 | 6 | 8 |
| % by wt of sodium hydroxide | to pH | to pH | to pH |
| Straightening performance | 3.0 | 3.5 | 4.0 |

From the table above, it was found that at similar pH values, the degree of straightening increased as the level of thiolactic acid increased.

C: Swatch evaluation using two different cellulose compounds as viscosity/thickening agent in aqueous on curly or wavy hair swatches (virgin hair, i.e., not chemically treated).

TABLE 6

| Viscosity agent | | |
|---|---|---|
| INCI US | Formula 1 % by weight | Formula 2 % by weight |
| SODIUM HYDROXIDE | 1 | 1 |
| THIOLACTIC ACID | 8 | 8 |
| HYDROXYETHYLCELLULOSE | 0.75 | — |
| METHYL HYDROXYETHYL-CELLULOSE (90% active) | — | 0.75 |
| WATER | 90.25 | 90.25 |

Both formulas above provided a more natural touch to the hair. Hydroxyethylcellulose. In addition, Formula 1 had better viscosity and the hair treated with this formula was easier to brush.

D: Swatch evaluation using different amounts of hydroxyethylcellulose in aqueous solutions on curly or wavy hair swatches (virgin hair, i.e., not chemically treated), Three aqueous solutions containing water, 8% by weight thiolactic acid, 3% by weight aminomethyl propanol, 2% by weight of silicone material comprising dimethicone and amodimethicone (KF 8020) and hydroxyethylcellulose at 0.75%, 1%, and 1.25% by weight were tested on hair swatches (all weights based on the total weight of the solutions).

The degrees of volume reduction and discipline (reduced or no frizz) observed on the treated swatches treated with compositions having from 0.75 to 1.25% by weight of hydroxyethylcellulose were comparable to each other.

It is to be understood that the foregoing describes preferred embodiments of the invention and that modifications may be made therein without departing from the spirit or scope of the invention as set forth in the claims.

The invention claimed is:

1. A composition for straightening hair comprising:
   (a) from 1% to 15% by weight of at least one reducing agent selected from thiolactic acid, thioglycolic acid, cysteine, cysteamine, homocysteine, glutathione, thioglycerol, thiomalic acid, thiodiglycol, dithiothreitol, thioxanthine, thiosalicylic acid, thiopropionic acid, lipoic acid, N-acetylcysteine and salts thereof, alkali metal sulfites, alkaline-earth metal sulfites, and mixtures thereof;
   (b) from 0.1% to 6.3% by weight of at least one neutralizing agent;
   (c) from 0.5% to 5% by weigh of at least one dimethicone copolyol;
   (d) from 0.1% to 2% by weight of at least one cellulose compound chosen from hydroxyalkyl cellulose, alkylcellulose, and mixtures thereof; and
   (e) water;
      wherein the pH of the composition ranges from 2 to 5.5, the composition is free of pyridine and derivatives thereof, and all weights are based on the total weight of the composition.

2. The composition, according to claim 1, wherein the at least one reducing agent is selected from the group consisting of thiolactic acid, thioglycolic acid, and salts thereof, and mixtures thereof.

3. The composition, according to claim 1, wherein the at least one neutralizing agent is selected from the group consisting of organic amines, alkali metal hydroxides, alkali earth metal hydroxides, alkali metal carbonates, alkali metal phosphates, and mixtures thereof.

4. The composition, according to claim 1, wherein the at least one neutralizing agent is selected from the group consisting of aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

5. The composition, according to claim 1, wherein the at least one neutralizing agent is sodium hydroxide present in an amount of from 0.1% to 4.1% by weight, based on the total weight of the composition.

6. The composition according to claim 1, wherein the at least one dimethicone copolyol is selected from the group consisting of oxypropylenated and/or oxyethylenated polydimethyl(methyl)siloxane, oxypropylenated and/or oxyethylenated polymethyl (C8-C22) alkyl dimethyl methyl siloxane, and mixtures thereof.

7. The composition according to claim 1, wherein the at least one dimethicone copolyol is selected from the group consisting of Dimethicone PEG-8 Benzoate, Dimethicone PEG-7 Phosphate, Dimethicone PEG-8 Phosphate, Dimethicone PEG-10 Phosphate, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-17/18 Dimethicone, cetyl PEG/PPG-10/1 dimethicone, and mixtures thereof.

8. The composition according to claim 1, wherein the at least one cellulose compound is hydroxyalkyl cellulose selected from the group consisting of hydroxyethylcellulose (also known as HEC), hydroxymethylcellulose, methylhydroxyethylcellulose, hydroxypropylcellulose (also known as HPC), hydroxybutylcellulose, hydroxyethylmethylcellulo se (also known as methyl hydroxyethylcellulose) and hydroxypropylmethylcellulose (also known as HPMC), cetyl hydroxyethylcellulose, and mixtures thereof.

9. The composition of claim 1, wherein the pH is from 2 to 5.

10. The composition of claim 1, wherein the pH of the composition ranges from 2 to 4.

11. The composition, according to claim 1, wherein the at least one reducing agent is thiolactic acid, salts thereof, or mixtures thereof.

12. The composition according to claim 1 comprising:
   a) from 3% to 10% by weight of least one reducing agent selected from thioglycolic acid, thiolactic acid, and mixtures thereof;
   b) from 0.2% to 5% by weight of aminomethyl propanol;
   c) from 1% to 4% by weight of at least one dimethicone copolyol;
   d) from 0.2% to 1% by weight of hydroxyethylcellulose; and
   e) water;
      wherein the composition is a gel, and the pH of the composition ranges from 2 to 5.5.

13. The composition of claim 12, wherein the pH is from 2 to 5.

14. The composition of claim 12, wherein the pH of the composition ranges from 2 to 4.

15. A process for shaping hair or altering the shape of hair, the process comprising the steps of:
   a) applying onto hair, a composition comprising:
      (a) from 1% to 15% by weight of at least one reducing agent selected from thiolactic acid, thioglycolic acid, cysteine, cysteamine, homocysteine, glutathione, thioglycerol, thiomalic acid, thiodiglycol, dithiothreitol, thioxanthine, thiosalicylic acid, thiopropionic acid, lipoic acid, N-acetylcysteine and salts thereof, alkali metal sulfites, alkaline-earth metal sulfites, and mixtures thereof;
      (b) from 0.1% to 6.3% by weight of at least one neutralizing agent;
      (c) from 0.5% to 5% by weigh of at least one dimethicone copolyol;
      (d) from 0.1% to 2% by weight of at least one cellulose compound selected from hydroxyalkyl cellulose, alkylcellulose, and mixtures thereof; and
      (e) water;
         wherein the pH of the composition ranges from 2 to 5.5, the composition is free of pyridine and derivatives thereof, and all weights are based on the total weight of the composition;

b) brushing the hair;

c) heating the hair to a temperature of at least 40° C.; while optionally applying a smoothing action on the hair; and d) rinsing the hair with water or contacting the hair with an intermediate agent having a neutral pH and selected from a shampoo, a conditioner, or both a shampoo and a conditioner, followed by rinsing with water.

16. The process according to claim 15, wherein the at least one neutralizing agent is selected from the group consisting of organic amines, alkali metal hydroxides, alkali earth metal hydroxides, alkali metal carbonates, alkali metal phosphates, and mixtures thereof.

17. The process according to claim 15, wherein step a) is preceded by (i) optionally, rinsing the hair with water while optionally applying a smoothing action on the hair; (ii) contacting the hair with a shampoo having a neutral pH; and (iii) rinsing the hair with water.

18. The process according to claim 15, wherein after applying the composition on the hair according to step a), the process further comprises a step of leaving the composition in step a) on the hair for a period of time of 5 to 30 minutes before brushing the hair according to step (2).

19. A method of making a composition for shaping or altering the shape of hair, the method comprising:

a) combining:
  (a) from 1% to 15% by weight of at least one reducing agent selected from thiolactic acid, thioglycolic acid, cysteine, cysteamine, homocysteine, glutathione, thioglycerol, thiomalic acid, thiodiglycol, dithiothreitol, thioxanthine, thiosalicylic acid, thiopropionic acid, lipoic acid, N-acetylcysteine and salts thereof, alkali metal sulfites, alkaline-earth metal sulfites, and mixtures thereof;
  (b) from 0.1% to 6.3% by weight of at least one neutralizing agent selected from organic amines, alkali metal hydroxides, alkali earth metal hydroxides, and mixtures thereof;
  (c) from 0.5% to 5% by weigh of at least one dimethicone copolyol;
  (d) from 0.1% to 2% by weight of at least one cellulose compound selected from hydroxyalkyl cellulose, alkylcellulose, and mixtures thereof; and
  (e) water;
    wherein composition is free of pyridine and derivatives thereof; and all weights are based on the total weight of the composition; and b) mixing (a) to (e) in order to form a composition having a pH ranging from 2 to 5.5.

* * * * *